US009829497B2

(12) United States Patent
Tatsutani et al.

(10) Patent No.: US 9,829,497 B2
(45) Date of Patent: Nov. 28, 2017

(54) SAMPLE ANALYSIS SYSTEM AND SAMPLE ANALYZER

(71) Applicant: Sysmex Corporation, Kobe-shi, Hyogo (JP)

(72) Inventors: Hiroo Tatsutani, Kobe (JP); Tomoyuki Asahara, Kobe (JP); Keisuke Kuwano, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 190 days.

(21) Appl. No.: 14/040,158

(22) Filed: Sep. 27, 2013

(65) Prior Publication Data

US 2014/0037502 A1 Feb. 6, 2014

Related U.S. Application Data

(63) Continuation of application No. PCT/JP2012/057977, filed on Mar. 27, 2012.

(30) Foreign Application Priority Data

Mar. 30, 2011 (JP) .................................. 2011-076740

(51) Int. Cl.
*G01N 35/00* (2006.01)
*G01N 35/02* (2006.01)

(52) U.S. Cl.
CPC . *G01N 35/00584* (2013.01); *G01N 35/00603* (2013.01); *G01N 35/026* (2013.01)

(58) Field of Classification Search
CPC ....... G01N 35/00603; G01N 35/00584; G01N 35/026

(Continued)

(56) References Cited

U.S. PATENT DOCUMENTS

2010/0066996 A1 3/2010 Kosaka et al.
2010/0112703 A1 5/2010 Tanaka
(Continued)

FOREIGN PATENT DOCUMENTS

JP 06-148202 A 5/1994
JP 2007-322243 A 12/2007
(Continued)

OTHER PUBLICATIONS

International Preliminary Report on Patentability for International Application No. PCT/JP2012/057977, dated Oct. 8, 2013, 10 pages.

(Continued)

*Primary Examiner* — Jill Warden
*Assistant Examiner* — Julie Tavares
(74) *Attorney, Agent, or Firm* — Brinks Gilson & Lione

(57) ABSTRACT

A sample analysis system includes a first measurement unit, a second measurement unit arranged to a downstream side of the first measurement unit, and an information processing section which obtains a measurement result of a sample. The information processing section determines, based on the measurement result of the sample measured by the first measurement unit, whether or not a retest of the sample by the first measurement unit is necessary. When the retest by the first measurement unit is necessary, the information processing section causes the sample container to be transported to a first sample supply position for the first measurement unit and causes the first measurement unit to perform measurement of the sample.

16 Claims, 10 Drawing Sheets

(58) Field of Classification Search
USPC .................................. 422/63–67; 436/43, 50
See application file for complete search history.

(56) References Cited

U.S. PATENT DOCUMENTS

| | | | |
|---|---|---|---|
| 2010/0159603 A1 | 6/2010 | Hamada et al. | |
| 2010/0166605 A1* | 7/2010 | Hamada ................. | G01N 35/02 422/65 |
| 2010/0212438 A1 | 8/2010 | Tanaka et al. | |
| 2010/0248374 A1 | 9/2010 | Kitagawa et al. | |
| 2011/0076193 A1 | 3/2011 | Kitagawa et al. | |
| 2011/0158851 A1* | 6/2011 | Kitagawa ............... | G01N 35/04 422/67 |

FOREIGN PATENT DOCUMENTS

| | | |
|---|---|---|
| JP | 2010-038659 A | 2/2010 |
| JP | 2010-107383 A | 5/2010 |
| JP | 2010-169663 A | 8/2010 |
| JP | 2010-190816 A | 9/2010 |
| JP | 2010-236952 A | 10/2010 |
| JP | 2011-075444 A | 4/2011 |
| JP | 2011-137749 A | 7/2011 |

OTHER PUBLICATIONS

International Search Report for International Application No. PCT/JP2012/057977, dated May 22, 2012, 2 pages.

* cited by examiner

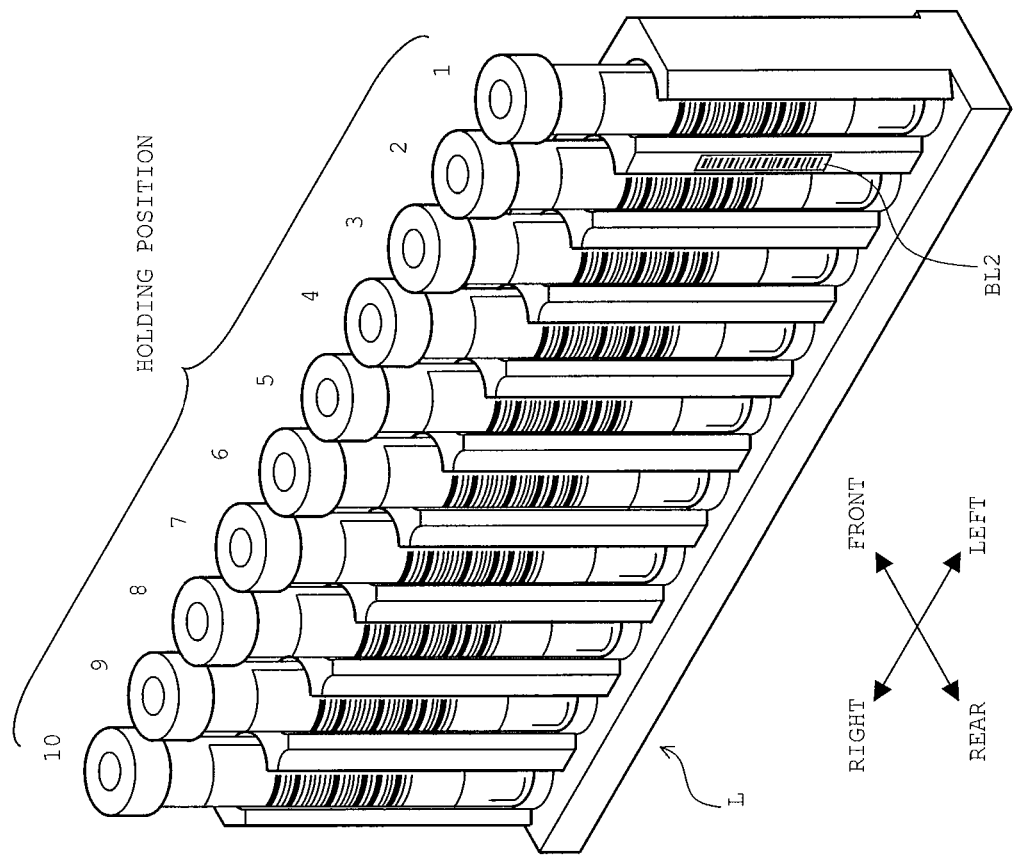
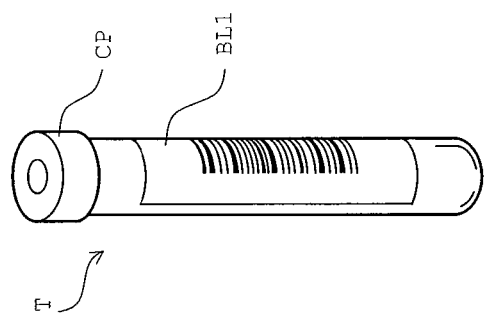

FIG. 7A

SAMPLE INFORMATION TABLE

| RACK ID | SAMPLE ID | HOLDING POSITION | NUMBER OF MEASUREMENTS | RESULT |
|---|---|---|---|---|
| ⋮ | ⋮ | 1 | 1 | FINAL |
| | ⋮ | 2 | 2 | FINAL |
| | ⋮ | 3 | 1 | FINAL |
| | ⋮ | 4 | 1 | NOT FINAL |
| | ⋮ | 5 | 1 | NOT FINAL |
| | ⋮ | 6 | 1 | NOT FINAL |
| | ⋮ | 7 | 0 | NOT FINAL |
| | ⋮ | 8 | 0 | NOT FINAL |
| | ⋮ | 9 | 0 | NOT FINAL |
| | ⋮ | 10 | 0 | NOT FINAL |

FIG. 7B

PRIORITY TABLE

PRIORITY ORDER HIGH ⟵⟶ PRIORITY ORDER LOW

| SAMPLE AT HOLDING POSITION 1 | SAMPLE AT HOLDING POSITION 2 | SAMPLE AT HOLDING POSITION 3 | SAMPLE AT HOLDING POSITION 4 | SAMPLE AT HOLDING POSITION 5 | SAMPLE AT HOLDING POSITION 6 | SAMPLE AT HOLDING POSITION 7 | SAMPLE AT HOLDING POSITION 8 | SAMPLE AT HOLDING POSITION 9 | SAMPLE AT HOLDING POSITION 10 |
|---|---|---|---|---|---|---|---|---|---|

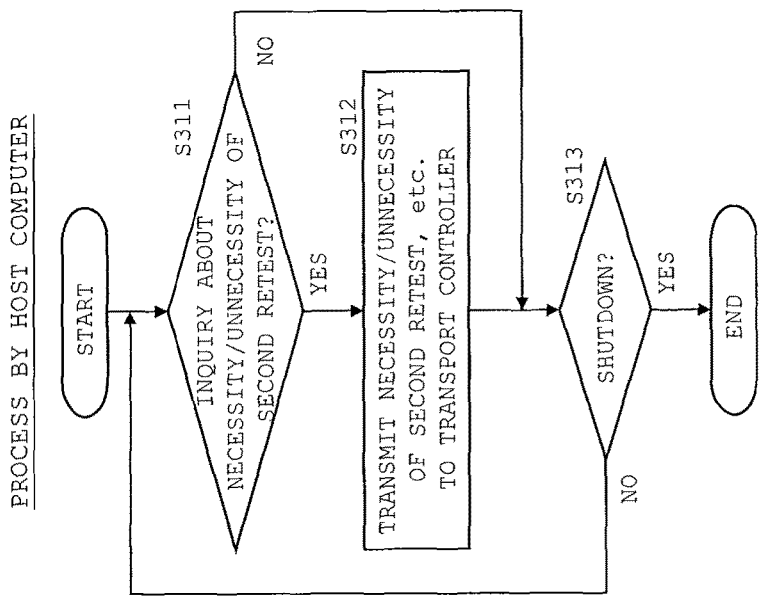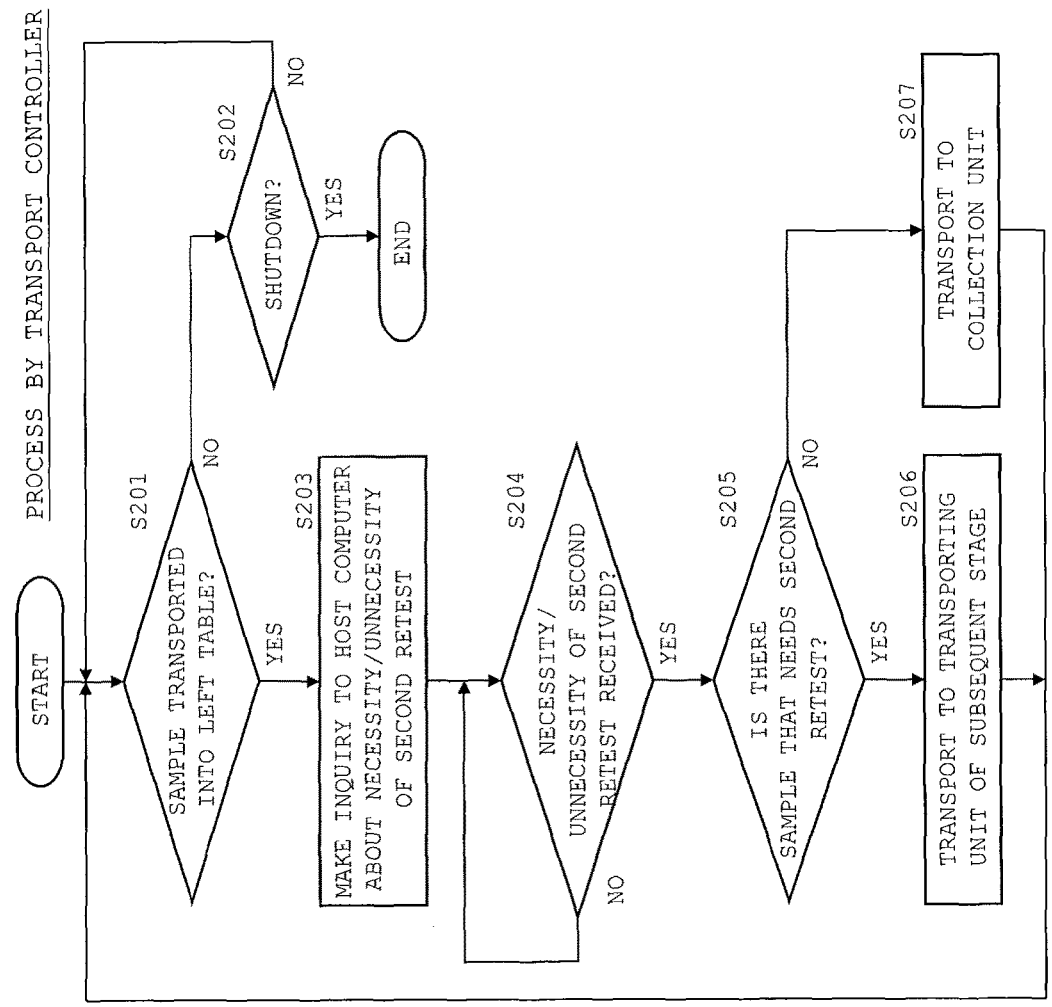

SAMPLE ANALYSIS SYSTEM AND SAMPLE ANALYZER

RELATED APPLICATIONS

This application is a continuation of PCT/JP2012/057977 filed on Mar. 27, 2012, which claims priority to Japanese Application No. 2011-076740 filed on Mar. 30, 2011. The entire contents of these applications are incorporated herein by reference.

BACKGROUND OF THE INVENTION

1. Field of the Invention

The present invention relates to a sample analysis system in which a plurality of measurement apparatuses for measuring samples in sample containers are arranged, and a sample analyzer used in the sample analysis system.

2. Disclosure of Related Art

To date, there are known sample testing systems in which samples are transported to a plurality of sample measurement apparatuses by use of a transporting apparatus, and retests are performed in the sample measurement apparatuses in accordance with measurement results of the samples.

For example, there is known a sample testing system which includes a plurality of measurement units which measure samples in sample containers, a plurality of sample transporting apparatuses respectively corresponding to the plurality of measurement units, and a test information management apparatus which receives measurement results obtained through sample measurements performed in the respective measurement units. Each sample transporting apparatus is configured to transport a sample rack holding a plurality of sample containers. Each sample transporting apparatus includes: a before-analysis rack holding section which holds sample racks holding sample containers before being subjected to measurement; a rack transport section which transports a sample rack received from the before-analysis rack holding section, to a sample supply position for supplying a sample to a measurement unit; and an after-analysis rack holding section which receives and holds a sample rack for which analysis has been completed, from the rack transport section.

In this sample testing system, until the test information management apparatus determines whether or not a retest of a sample whose first measurement (first-round test) has been completed is necessary, the sample rack holding the sample is caused to wait in the rack transport section, and when a retest is necessary, the sample rack is returned to the sample supply position.

However, in this sample testing system, the test information management apparatus determines whether or not a retest of a sample is necessary, with respect to each of all measurement items for which a retest could be necessary. This may take time before such determination is completed. Therefore, there are cases where a sample rack is caused to wait in the rack transport section for a long time, which makes it difficult for the rack transport section to transport another sample rack during that time. This may result in reduced sample processing efficiency.

SUMMARY OF THE INVENTION

A first aspect of the present invention relates to a sample analysis system. The sample analysis system according to this aspect includes: a first measurement unit; a second measurement unit arranged to a downstream side of the first measurement unit; a transporting apparatus including a first transport section arranged corresponding to the first measurement unit and a second transport section arranged corresponding to the second measurement unit; and an information processing section which obtains a measurement result of a sample measured by the first or second measurement unit. Here, the first transport section includes a first transport path for transporting a sample container to a first sample supply position for the first measurement unit and a sending-out part for sending out a sample container to the downstream side. Further, the second transport section includes a second transport path for transporting a sample container sent out from an upstream side to a second sample supply position for the second measurement unit. The information processing section determines, based on the measurement result of the sample measured by the first measurement unit, whether or not a retest of the sample by the first measurement unit is necessary, and performs, when the retest by the first measurement unit is necessary, a process of causing a sample container containing the sample to be transported to the first sample supply position through the first transport path of the first transport section, and of causing the first measurement unit to perform measurement of the sample.

A second aspect of the present invention relates to a sample analyzer capable of transmitting a measurement result of a sample to a test information management apparatus which manages test information regarding a test of a sample. The sample analyzer according to this aspect includes: a measurement unit which measures a sample; a transport section which includes a transport path for transporting a sample container to a sample supply position for the measurement unit, and a sending-out part for sending out the sample container to a sample analyzer on a downstream side; and an information processing section which obtains a measurement result of the sample measured by the measurement unit. Here, the information processing section determines whether or not a retest of the sample by the measurement unit is necessary, based on the measurement result of the sample; causes, when the retest by the measurement unit is necessary, the sample container to be transported to the sample supply position through the transport path and causes the measurement unit to perform measurement of the sample; makes, when the retest by the measurement unit is unnecessary, an inquiry to the test information management apparatus about whether or not a retest of the sample by a sample analyzer on the downstream side is necessary; and causes, when having received a determination result indicating that the retest of the sample is necessary from the test information management apparatus, the sending-out part to send out the sample container to the sample analyzer on the downstream side.

BRIEF DESCRIPTION OF THE DRAWINGS

The above and other objects and new features of the present invention will be fully clarified by the following description of the embodiment, when read in conjunction with accompanying drawings.

FIGS. 2A and 2B respectively show structures of a sample container and a sample rack according to an embodiment;

FIGS. 7A and 7B respectively show concepts of configurations of a sample information table and a priority table according to an embodiment;

FIG. 10A is a flow chart showing a process performed by a transport controller when a sample rack is transported into a left table, and FIG. 10B is a flow chart showing a process of transmitting necessity/unnecessity of a second retest performed by a host computer, according to an embodiment.

Figure 1:
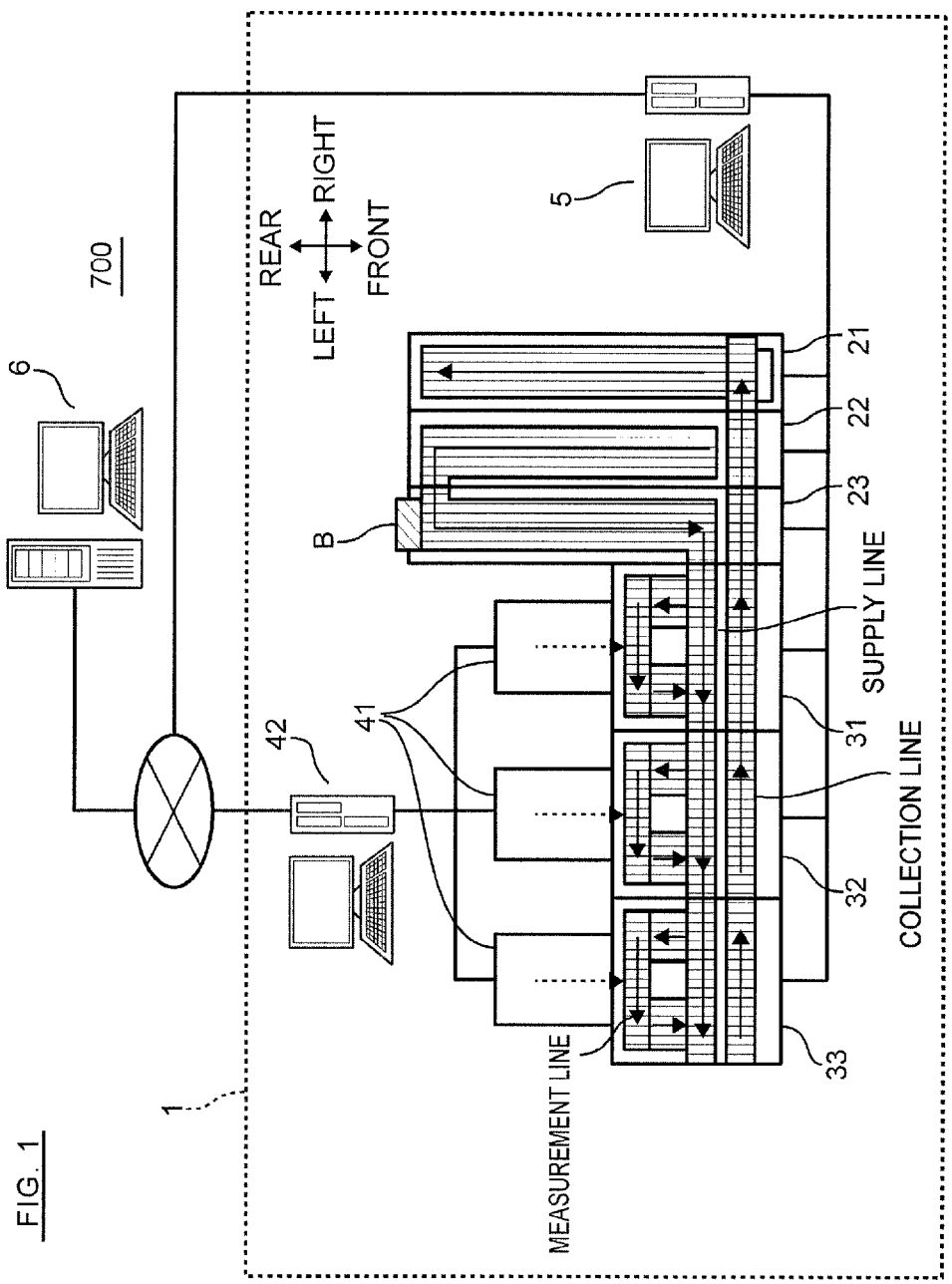
FIG. 1 schematically shows a structure of a sample analysis system according to an embodiment, viewed from above.

It should be noted that the drawings are solely for description and do not limit the scope of the present invention by any degree.

DETAILED DESCRIPTION OF PREFERRED EMBODIMENTS

The present embodiment is realized by applying the present invention to a sample analysis system for performing tests and analyses regarding blood. Hereinafter, the present embodiment will be described with reference to the drawings.

In the present embodiment, a preprocessing unit 23 corresponds to the "transporting-in unit" described in claims. When a measurement unit 41 at the right end and a measurement unit 41 at the left end in FIG. 1 respectively correspond to the "first measurement unit" and the "second measurement unit" in claims, a measurement unit 41 in the middle corresponds to the "third measurement unit" described in claims. In this case, transporting unit 31 and transporting unit 33 respectively correspond to the "first transport section" and the "second transport section" described in claims, and a transporting unit 32 corresponds to the "third transport section" described in claims. Further, in this case, a right table 310 and a rack transporter 320 of the transporting unit 31 correspond to the "first transport path" described in claims, a right table 310 and a rack transporter 320 of the transporting unit 33 correspond to the "second transport path" described in claims. Further, in this case, a belt 341b of the transporting units 31 corresponds to the "sending-out part" described in claims, and a left table 330 of the transporting units 31 corresponds to the "retaining part" described in claims. Further, in this case, a rack sending-in mechanism 333 of the transporting units 31 corresponds to the "transporting-out part" described in claims, a rack transporter 340 of the transporting units 31 corresponds to the "third transport path" described in claims, and a rack pushing-out mechanism 342 of the transporting units 31 corresponds to the "container transfer part" described in claims. A rack transporter 350 corresponds to the "fourth transport path" described in claims. An information processing unit 42 corresponds to the "information processing section" and the "first determination controller" described in claims. A transport controller 5 corresponds to the "information processing section" and the "second determination controller" described in claims. A host computer 6 corresponds to the "test information management apparatus" described in claims. However, the above correspondence between the claims and the present embodiment is merely an example, and does not limit the claims to the present embodiment.

FIG. 1 schematically shows a structure of a sample testing system 700, which includes a sample analysis system 1, viewed from above. The sample analysis system 1 according to the present embodiment includes a collection unit 21, a feeding unit 22, a preprocessing unit 23, transporting units 31 to 33, three measurement units 41, an information processing unit 42, and a transport controller 5. Moreover, the sample testing system 700 includes a host computer 6, wherein the sample analysis system 1 of the present embodiment is communicably connected to the host computer 6 via a communication network.

The collection unit 21, the feeding unit 22, and the preprocessing unit 23 are arranged adjacent to each other in the left-right direction as shown in FIG. 1 such that a sample rack L can be transported therebetween. Further, each of these units is configured such that a plurality of sample racks L, each being capable of holding ten sample containers T, can be placed thereon.

FIGS. 2A and 2B respectively show structures of a sample container T and a sample rack L. FIG. 2A is a perspective view showing an external view of the sample container T, and FIG. 2B is a perspective view showing an external view of the sample rack L holding ten sample containers T. FIG. 2B also shows the orientation (front, rear, left, and right shown in FIG. 1) of the sample rack L when it is placed on the feeding unit 22.

With reference to FIG. 2A, the sample container T is a tubular container made of glass or synthetic resin having translucency, and its upper end is open. A blood sample collected from a patient is contained in the sample container T, and the opening at the upper end of the sample container T is sealed with a cap CP. A bar code label BL1 is attached to a lateral surface of the sample container T. A bar code indicating a sample ID is printed on the bar code label BL1.

With reference to FIG. 2B, ten holders are formed in the sample rack L at holding positions 1 to 10, so as to be able to align and hold ten sample containers T vertically (in a standing sate). Further, a bar code label BL2 is attached to a lateral surface on the rear side of the sample rack L. A bar code indicating a rack ID is printed on the bar code label BL2.

With reference back to FIG. 1, the collection unit 21 houses sample racks L collected through a collection line described later.

The feeding unit 22 houses sample racks L fed by a user, and transports out each sample rack L housed therein, to the preprocessing unit 23. When starting measurement of samples, the user sets sample containers T respectively containing samples, in a sample rack L, and places this sample rack L on the feeding unit 22, first. Then, this sample rack L is sequentially transported to units on the downstream side (left side), to be measured.

The preprocessing unit 23 reads, by means of a bar code unit B, a rack ID of the sample rack L transported out from the feeding unit 22 and sample IDs of the sample containers T associated with respective holding positions in the sample rack L. Then, the preprocessing unit 23 transmits information read by the bar code unit B to the transport controller 5, and transports out the sample rack L for which the reading has been completed, to the transporting unit 31.

As shown in FIG. 1, the transporting units 31 to 33 are arranged adjacent to each other in the left-right direction such that a sample rack L can be transported therebetween. The right end of the transporting unit 31 is connected to the preprocessing unit 23 such that a sample rack L can be transported therebetween. As shown in FIG. 1, the transporting units 31 to 33 are arranged to the front of the three measurement units 41, respectively.

As shown in FIG. 1, each of the transporting units 31 to 33 is provided with two transport lines, each of which is selected depending on whether a sample rack L is transported or not to its corresponding measurement unit 41. That is, in a case where measurement is performed by a measurement unit 41, a sample rack L is transported along a "measurement line" indicated by a left arrow in the rear part. In a case where no measurement is performed by the measurement unit 41 and a measurement is performed on the downstream side (left side), the sample rack L is transported along a "supply line" indicated by a left arrow in the middle part, so as to skip the measurement unit 41. Further, as shown in FIG. 1, each of the transporting units 31 to 33 is provided with a rightward transport line for transporting a sample rack L to the collection unit 21. That is, a sample rack L that no longer needs to be subjected to measurement on the downstream side is transported along a "collection line" indicated by a right arrow in the front part, to be collected in the collection unit 21.

Each of the three measurement units 41 takes out a sample container T from a sample rack L, at a predetermined position (indicated by the dotted arrow in FIG. 1) on the measurement line of its corresponding one of the transporting units 31 to 33 which are respectively arranged to the front of the three measurement units 41, and measures the sample contained in this sample container T. Specifically, each measurement unit 41 moves the sample container T taken out from the sample rack L rearward to take it inside, aspirates the sample contained in this sample container T, and measures the aspirated sample. Each measurement unit 41 includes an optical detector for performing optical measurement on a sample. To this optical detector, a measurement specimen prepared from a sample and predetermined reagents is supplied, whereupon the optical detector detects, as data of that sample, optical information (side fluorescence signal, forward scattered light signal, and side scattered light signal) from each blood cell in the measurement specimen. The data of the sample obtained by the measurement unit 41 is analyzed by the information processing unit 42, and a measurement result such as red blood cell count and white blood cell count, is generated. When measurement in the measurement unit 41 has been completed, the measurement unit 41 returns this sample container T to its original holder in the sample rack L.

The information processing unit 42 is communicably connected to the three measurement units 41, and controls operation of the three measurement units 41. The information processing unit 42 obtains data of the samples obtained by the three measurement units 41, and performs an analysis process. Further, the information processing unit 42 is communicably connected to the host computer 6 via the communication network, and transmits measurement results generated through the analysis process, to the host computer 6.

The transport controller 5 controls transporting operation of the collection unit 21, the feeding unit 22, the preprocessing unit 23, and sample relaying sections 3a (see FIG. 4) of the transporting units 31 to 33. Further, the transport controller 5 is communicably connected to the host computer 6 via the communication network. When the transport controller 5 has received the sample IDs from the preprocessing unit 23, the transport controller 5 makes an inquiry about measurement orders to the host computer 6. Thereafter, based on the measurement orders received from the host computer 6, the transport controller 5 determines a transport destination of the sample rack L transported out from the preprocessing unit 23, and controls the sample relaying sections 3a (see FIG. 4) of the transporting units 31 to 33 such that the sample rack L is transported to the transport destination.

Here, in the present embodiment, among the three measurement units 41, the measurement units 41 at the right end and in the middle can perform measurement regarding a CBC item and a DIFF item. The measurement unit 41 at the left end can perform measurement regarding the CBC item, the DIFF item, and a RET item. The CBC item includes WBC (white blood cell), RBC (red blood cell), PLT (platelet), HGB (hemoglobin), and the like. The DIFF item includes MONO (monocyte), EO (eosinophil), BASO (basophil), NEUT (neutrophil), LYMPH (lymphocyte), and the like. The RET item includes RET (reticulocyte) and the like. Therefore, in a case where only the CBC item and the DIFF item are included in the measurement orders of the samples held in a sample rack L, this sample rack L is transported to the measurement unit 41 at the right end or in the middle. In a case where the RET item is included in the measurement orders of the samples held in a sample rack L, this sample rack L is transported to the measurement unit 41 at the left end. When the sample rack L is transported to its transport destination measurement unit 41, the first measurement (hereinafter, referred to as "first-round test") of each sample is performed by the measurement unit 41. The information processing unit 42 analyzes data of each sample obtained by the measurement unit 41, and generates a measurement result such as white blood cell count, red blood cell count, platelet count, hemoglobin concentration, monocyte count, reticulocyte count, and the like.

Further, in the present embodiment, there may be a case where measurement is performed again based on the measurement result of the first-round test. The measurement in this case (hereinafter, referred to as "retest") includes a retest (hereinafter, referred to as "first retest") to be performed by the measurement unit 41 that performed the first-round test, and a retest (hereinafter, referred to as "second retest") to be performed on the downstream side (left side) relative to the measurement unit 41 that performed the first-round test. The procedure of determining whether a first retest is necessary and the procedure of determining whether a second retest is necessary will be described later with reference to FIGS. 8, 9A, and 9B.

Figure 3:
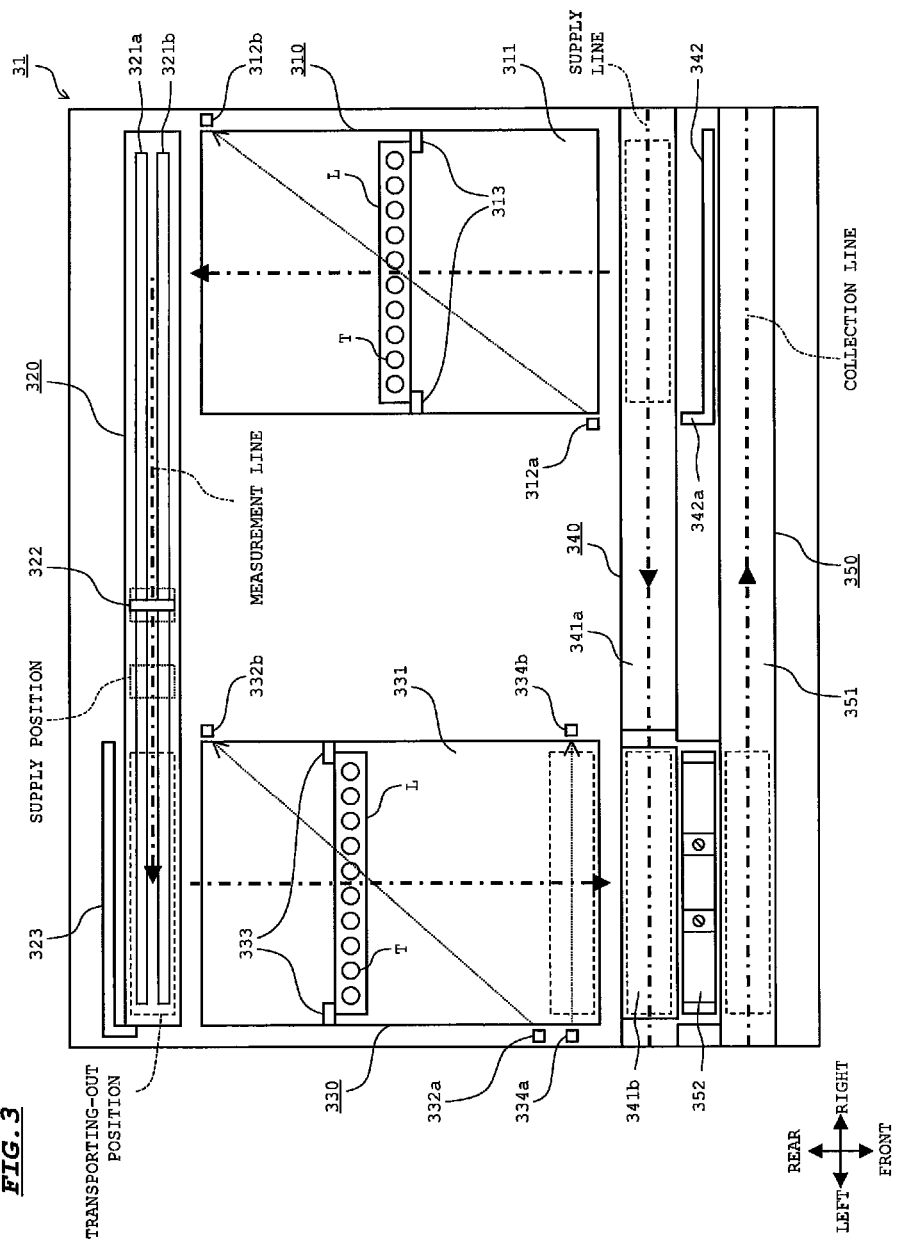
FIG. 3 shows a structure of a transporting unit according to an embodiment, viewed from above.

FIG. 3 shows a structure of the transporting unit 31 viewed from above. It should be noted that the transporting units 32 and 33 are structured similarly to the transporting unit 31.

The transporting unit 31 includes a right table 310, a rack transporter 320, a left table 330, and rack transporters 340 and 350. The rack transporter 320 forms the measurement line shown in FIG. 1. The rack transporter 340 forms the supply line shown in FIG. 1, and the rack transporter 350 forms the collection line shown in FIG. 1.

In a case where measurement on the sample rack L transported out from the upstream side (right side) is not performed by the measurement unit 41 corresponding to the transporting unit 31, this sample rack L is linearly sent by belts 341a and 341b of the rack transporter 340, along the supply line from the right end to the left end of the rack transporter 340. Then, this sample rack L is transported out to the transporting unit 32 on the downstream side (left side) by the belt 341b of the rack transporter 340.

Next, in a case where measurement on the sample rack L transported out from the upstream side (right side) is performed by the measurement unit 41 corresponding to the transporting unit 31, this sample rack L is located at a right end position of the rack transporter 340. That is, a rack pushing-out mechanism 342 is moved rearward such that a wall portion 342a slightly protrudes on the supply line from the state shown in FIG. 3, with the belt 341a being driven. Accordingly, the sample rack L transported out from the upstream side stops, abutting against the wall portion 342a, to be located at the right end position of the rack transporter 340. Subsequently, by the rack pushing-out mechanism 342 being moved further rearward, this sample rack L is pushed out to a front position of a transport path 311 of the right table 310.

It should be noted that, when the sample rack L is pushed out to the front position of the transport path 311, the transport controller 5 transmits the rack ID of this sample rack L and the sample IDs of the sample containers T held in this sample rack L, to the information processing unit 42.

When the sample rack L pushed out onto the transport path 311 is detected by transmissive-type sensors 312a and 312b, a rack sending-in mechanism 313 moves rearward, engaged with the front end of the sample rack L, whereby the sample rack L is sent rearward. In this manner, the sample rack L is sent into a right end position of the rack transporter 320.

Belts 321a and 321b of the rack transporter 320 are configured to be able to be independently driven by different stepping motors (not shown). Each of the belts 321a and 321b can be driven both leftward and rightward. Further, each of the belts 321a and 321b is provided with two projecting pieces (not shown) having an interval therebetween that is slightly greater than the width in the left-right direction of the sample rack L. The sample rack L on the rack transporter 320 can be transported leftward and rightward along the measurement line, by being held by the projecting pieces of the belt 321a or the projecting pieces of the belt 321b. When the sample rack L is located at the right end position of the rack transporter 320, the sample rack L is transported leftward along the measurement line by the belt 321a or the belt 321b.

When the sample rack L is transported leftward from the right end position of the rack transporter 320 and thus a sample container T passes a position immediately below a contact-type container sensor 322, a contact piece of the container sensor 322 is bent by the sample container T. Accordingly, the holding position in the sample rack L at which the sample container T is held is detected.

When the sample container T detected by the container sensor 322 is located at a supply position, a hand part (not shown) of the measurement unit 41 takes out this sample container T from the sample rack L. The taken out sample container T is used for measurement within the measurement unit 41, and then returned to the sample rack L again. It should be noted that while the sample container T is in the measurement unit 41, the sample rack L is transported on the transport line leftward and rightward, and existence of sample containers T at other holding positions is detected by the container sensor 322, as appropriate.

Here, as described above, when measurement is performed in the measurement unit 41, the information processing unit 42 performs the analysis process based on the data of the sample obtained by the measurement unit 41. Based on a measurement result generated through the analysis process, the information processing unit 42 determines whether or not it is necessary (necessity/unnecessity) to perform measurement (first retest) in the measurement unit 41 again on the sample, which is the source of the measurement result. When it has been determined that a first retest is necessary, the sample rack L is transported rightward along the measurement line. Then, the sample container T, which has become the target of the first retest, is located at the supply position again, and measurement (first retest) is performed in the measurement unit 41 again with respect to this sample container T.

In this manner, among the sample containers T held in the sample rack L, with respect to all the sample container(s) T which have become the target for measurement by this measurement unit 41, when measurement and necessary first retests have all been completed, the sample rack L is sent by the belt 321a or 321b to a "transporting-out position" at the left end of the rack transporter 320. Then, the sample rack L is pushed out by a rack pushing-out mechanism 323, to a rear position of a transport path 331 of the left table 330.

When the sample rack L pushed out onto the transport path 331 is detected by transmissive-type sensors 332a and 332b, a rack sending-in mechanism 333 moves forward, engaged with a rear end of the sample rack L, whereby the sample rack L is sent forward. Accordingly, the sample rack L is sent into a front position of the left table 330. In the vicinity of the front position of the left table 330, transmissive-type sensors 334a and 334b are provided. The sample rack L located at the front position of the left table 330 is detected by the sensors 334a and 334b.

Here, when the sample rack L is located on the transport path 331, with respect to each sample held in this sample rack L, the transport controller 5 makes an inquiry to the host computer 6, about necessity/unnecessity of measurement (second retest) to be performed again by a measurement unit 41 of the subsequent stage. Based on the measurement result and the like received from the information processing unit 42, the host computer 6 has determined in advance necessity/unnecessity of a second retest by the measurement unit 41 of the subsequent stage, and transmits necessity/unnecessity of a second retest in response to the inquiry from the transport controller 5. In a case where a second retest is necessary for one or more samples among the samples held in the sample rack L, this sample rack L is transported to the downstream side (left side). On the other hand, in a case where a second retest is necessary for none of the samples held in this sample rack L, this sample rack L is transported to the upstream side (right side) along the collection line.

It should be noted that, in the present embodiment, when a sample rack L is located in the left table 330 in either of the right two transporting units 31 and 32, if it is determined that a second retest is necessary, this sample rack L is transported out to the transporting unit on the downstream side (left side), and the second retest is performed by the measurement unit 41 at the left end. Further, when a sample rack L is located in the left table 330 of the leftmost (most downstream) transporting unit 33, necessity/unnecessity of a second retest is not determined and this sample rack L is transported to the upstream side (right side) along the collection line.

Subsequently, a separator 352 which is provided to the front of the left table 330 and between the rack transporters 340 and 350 is controlled so as to be opened and closed, and the sample rack L is located at a left end position of the rack transporter 340 or a left end position of the rack transporter 350.

In a case where the sample rack L is to be transported to a measurement unit 41 on the downstream side (left side), the sample rack L is moved by the rack sending-in mechanism 333 to the left end position of the rack transporter 340, with the rack transporter 340 and 350 separated from each other by the separator 352. Then, this sample rack L is transported out to the transporting unit 32 on the downstream side by the belt 341b of the rack transporter 340.

On the other hand, in a case where the sample rack L is not to be transported to a measurement unit 41 on the downstream side (left side), the upper surface of the separator 352 is lowered to the same level as that of the upper surface of the belt 341b of the rack transporter 340. Then, the sample rack L is moved to the left end position of the rack transporter 350, across the rack transporter 340, by the rack sending-in mechanism 333. Subsequently, this sample rack L is linearly sent by a belt 351 of the rack transporter 350, from the left end to the right end of the rack transporter 350 along the collection line, and is transported out to the preprocessing unit 23 arranged to the upstream side (right side) of the transporting unit 31. In this manner, the sample rack L transported rightward along the collection line is finally housed in the collection unit 21.

Figure 4:
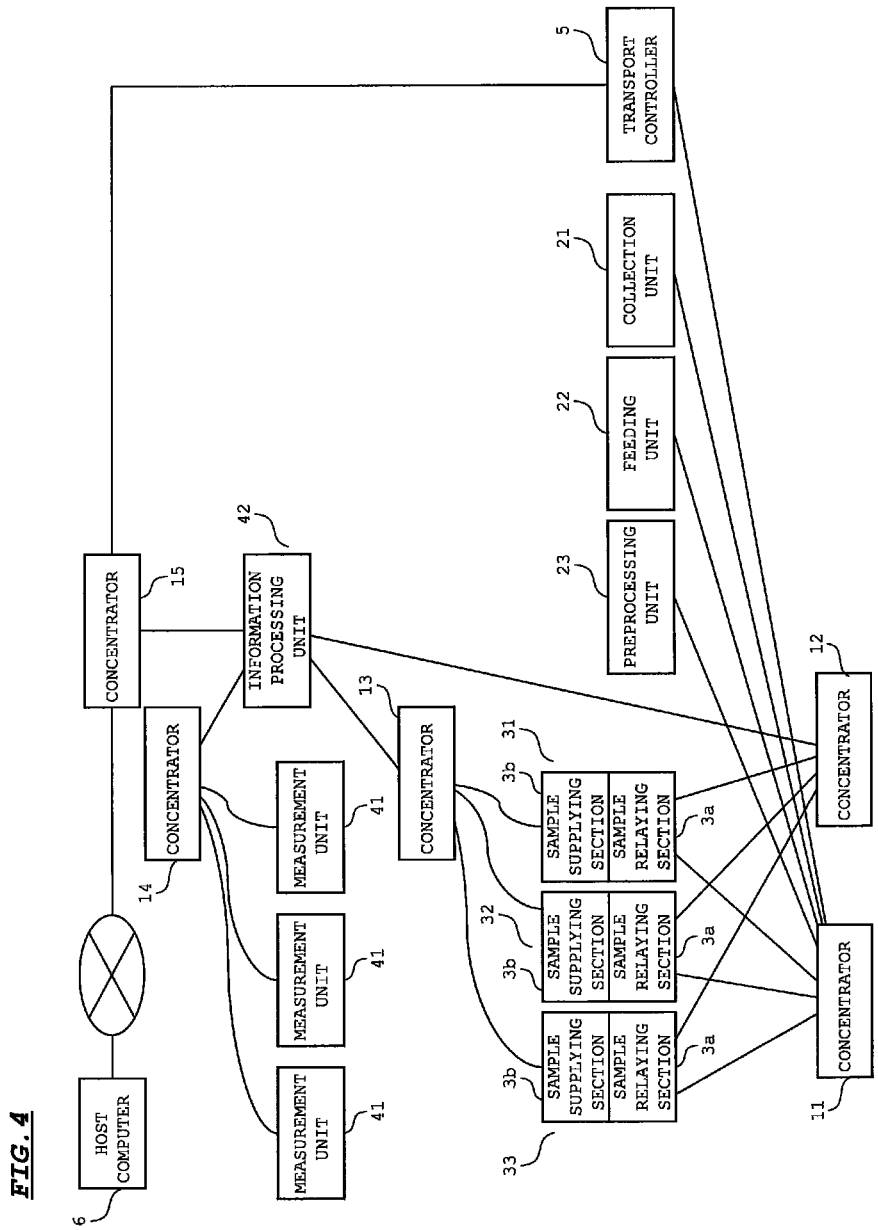
FIG. 4 schematically shows mutual connection relationship among units and apparatuses in a sample analysis system according to an embodiment.

FIG. 4 schematically shows mutual connection relationship among units and apparatuses in the sample analysis system 1.

Here, each of the transporting units 31 to 33 is shown divided into the sample relaying section 3a and a sample supplying section 3b. Specifically, the sample relaying section 3a is a portion that includes the left table 330 and the rack transporters 340 and 350 shown in FIG. 3, and receives a sample rack L from one of two adjacent transporting units and transports the sample rack L to the other transporting unit. The sample supplying section 3b is a portion that includes the right table 310 and the rack transporter 320 shown in FIG. 3, and transports a sample rack L to the supply position for measurement of a sample by the measurement unit 41.

To a concentrator 11, the collection unit 21, the feeding unit 22, the preprocessing unit 23, the three sample relaying sections 3a, and the transport controller 5 are communicably connected. To a concentrator 12, the three sample relaying sections 3a and the information processing unit 42 are communicably connected. To a concentrator 13, the three sample supplying sections 3b and the information processing unit 42 are communicably connected. To a concentrator 14, the three measurement units 41 and the information processing unit 42 are communicably connected. To a concentrator 15, the information processing unit 42, the transport controller 5, and the host computer 6 via the communication network are communicably connected.

Figure 5:
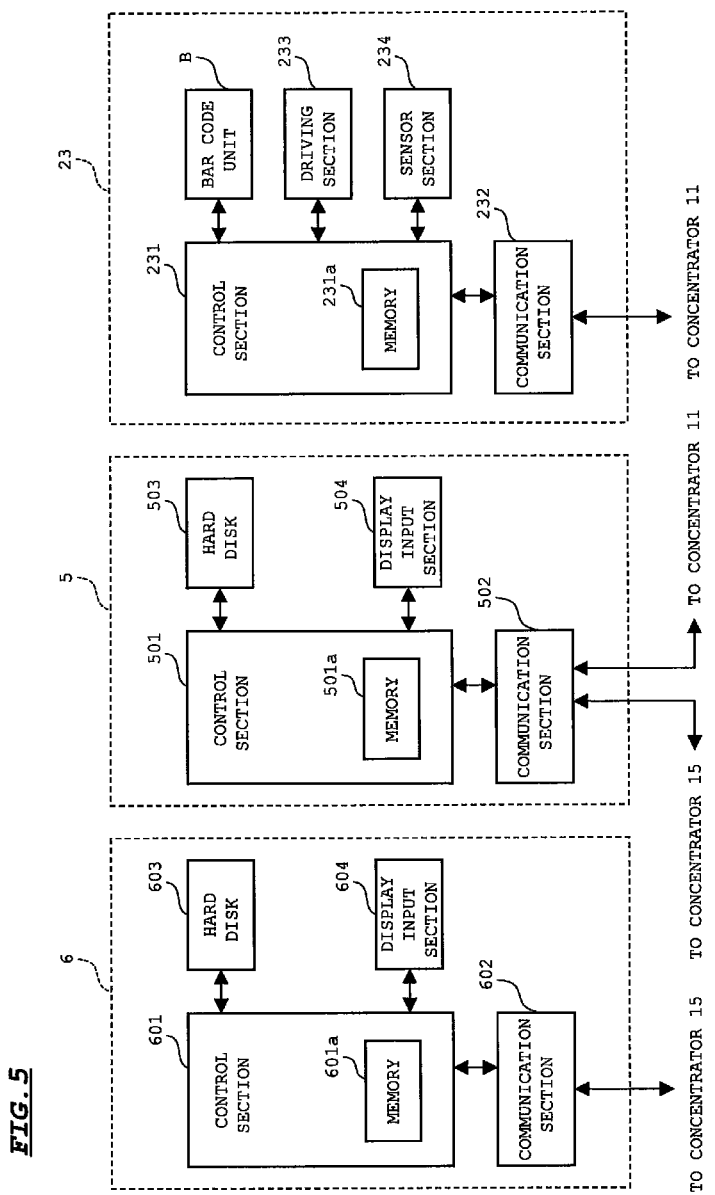
FIG. 5 is a schematic diagram of configurations of a transport controller, a host computer, and a preprocessing unit according to an embodiment.

FIG. 5 is a schematic diagram of configurations of the transport controller 5, the host computer 6, and the preprocessing unit 23.

The transport controller 5 includes a control section 501, a communication section 502, a hard disk 503, and a display input section 504.

The control section 501 includes a memory 501a. The control section 501 controls the collection unit 21, the feeding unit 22, the preprocessing unit 23, and the sample relaying sections 3a of the transporting units 31 to 33, by executing computer programs stored in the memory 501a or in the hard disk 503. The communication section 502 includes a communication interface for performing data communication with external apparatuses based on Ethernet (registered trademark) standard, and performs data communication with the concentrators 11 and 15.

The hard disk 503 has stored therein computer programs for controlling target apparatuses. The display input section 504 includes a display and an input device. The display input section 504 displays an image on the display based on video signals outputted from the control section 501, and receives inputs from the user via the input device.

The host computer 6 has a configuration similar to that of the transport controller 5, and includes a control section 601, a communication section 602, a hard disk 603, and a display input section 604. The hard disk 603 has stored therein test information that includes past measurement results, disease information, and the like of a plurality of subjects, and all measurement items that can be measured by the three measurement units 41.

The preprocessing unit 23 includes a control section 231, a communication section 232, a driving section 233, a sensor section 234, and the bar code unit B.

The control section 231 includes a memory 231a. The control section 231 controls components in the preprocessing unit 23, by executing computer programs stored in the memory 231a in the control section 231 in accordance with an instruction from the control section 501 of the transport controller 5. The communication section 232 performs data communication with the concentrator 11, similarly to the communication section 502 of the transport controller 5.

Information read by the bar code unit B is outputted to the control section 231. The control section 231 stores the information received from the bar code unit B in the memory 231a, and transmits the information to the transport controller 5 via the communication section 232. The driving section 233 includes mechanisms for transporting a sample rack L on the preprocessing unit 23. The sensor section 234 includes sensors for detecting a sample rack L on the preprocessing unit 23.

Since the collection unit 21 and the feeding unit 22 have a configuration equivalent to that of the preprocessing unit 23 from which the bar code unit B is omitted, their configuration is not shown or described here for convenience.

Figure 6:
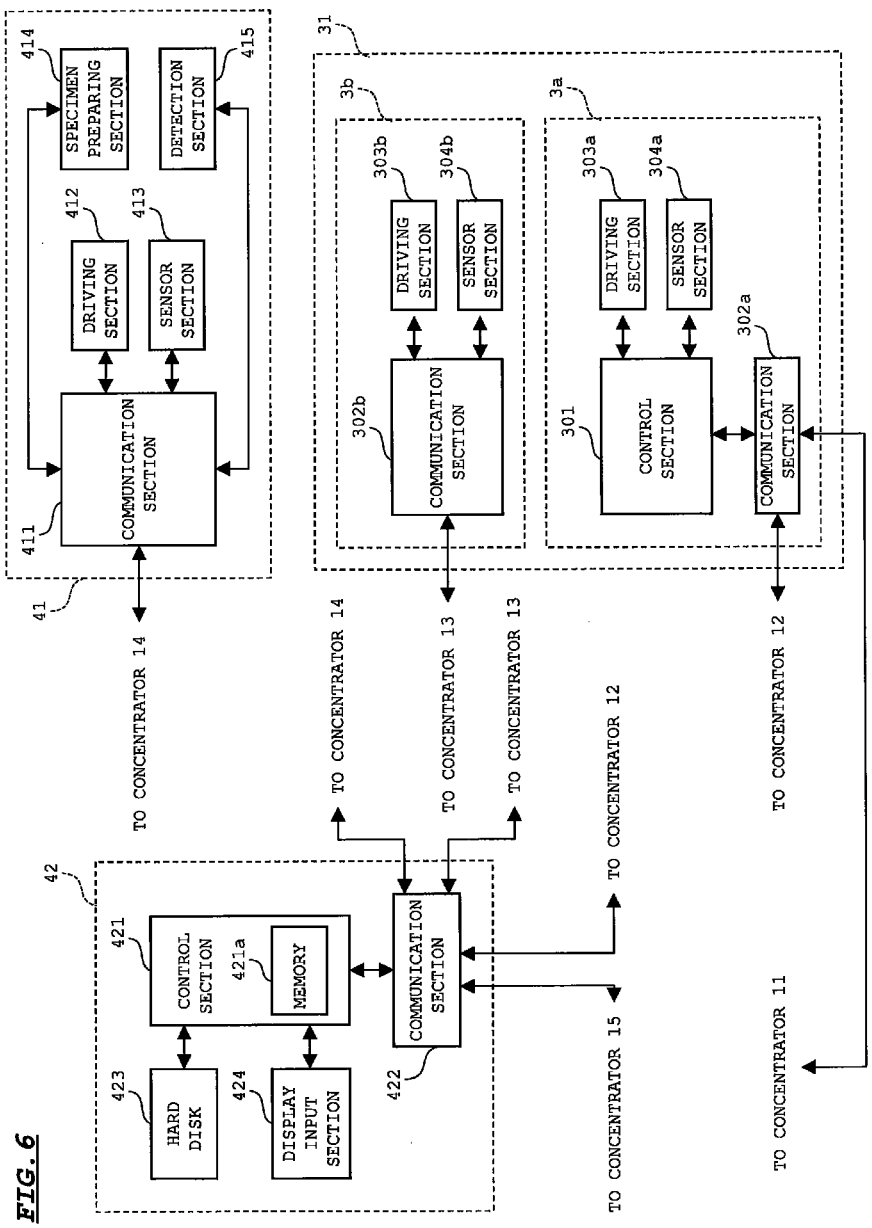
FIG. 6 is a schematic diagram of configurations of a transporting unit, a measurement unit, and an information processing unit according to an embodiment.

FIG. 6 is a schematic diagram of configurations of the transporting unit 31, a measurement unit 41, and the information processing unit 42. Although only the transporting unit 31 and one of the measurement units 41 are shown FIG. 6 for convenience, the configurations of the transporting units 32 and 33 and the other measurement units 41 are similar to those shown in FIG. 6.

The transporting unit 31 has a configuration equivalent to that of the preprocessing unit 23 shown in FIG. 5, from which the bar code unit B is omitted and to which a communication section 302b, a driving section 303b, and a sensor section 304b are added.

A communication section 302a performs data communication with the concentrators 11 and 12, and the communication section 302b performs data communication with the concentrator 13. A driving section 303a is controlled by a control section 301, and the driving section 303b is controlled by the information processing unit 42 via the communication section 302b. A sensor section 304a outputs a detection signal to the control section 301 and the sensor section 304b outputs a detection signal to the information processing unit 42 via the communication section 302b.

The communication section 302b, the driving section 303b, and the sensor section 304b are included in the sample supplying section 3b shown in FIG. 4. Components of the transporting unit 31 other than the communication section 302b, the driving section 303b, and the sensor section 304b are included in the sample relaying section 3a shown in FIG. 4. The driving section 303a and the sensor section 304a respectively include mechanisms for transporting and detecting a sample rack L on the left table 330 and the rack transporters 340 and 350 shown in FIG. 3. The driving section 303b and the sensor section 304b respectively include mechanisms for transporting and detecting a sample rack L on the right table 310 and the rack transporter 320 shown in FIG. 3.

The measurement unit 41 includes a communication section 411, a driving section 412, a sensor section 413, a specimen preparing section 414, and a detection section 415.

The communication section 411 performs data communication with the concentrator 14, similarly to the communication section 302b of the transporting unit 31. The driving section 412 includes mechanisms for performing sample measurement. The sensor section 413 includes sensors for detecting a position of a sample container T, and the like. The specimen preparing section 414 mixes and stirs reagents and a sample aspirated in the measurement unit 41 together, to prepare a specimen for measurement. The detection section 415 measures the specimen prepared by the specimen preparing section 414. Data of the sample obtained through such measurement is transmitted to the information processing unit 42 via the communication section 411, and is subjected to an analysis process in the information processing unit 42.

The information processing unit 42 has a configuration similar to that of the transport controller 5 shown in FIG. 5.

A control section 421 controls components of the transporting unit 31 and receives detection signals from the sensor section 304b, via a communication section 422 and the concentrator 13. Further, the control section 421 controls components of the measurement unit 41 and receives detection signals from the sensor section 413 and data of samples measured by the detection section 415, via the communication section 422 and the concentrator 14. A hard disk 423 has stored therein information regarding measurements (sample information table) performed by the measurement unit 41, and information regarding priority orders (priority table) of samples to be supplied to the measurement unit 41. The sample information table and the priority table are set for each measurement unit 41.

FIG. 7A shows a concept of a configuration of the sample information table.

In the sample information table, there set are: a rack ID item in which to store a rack ID; a sample ID item in which to store a sample ID; a holding position item in which to store a holding position in a sample container T; a number-of-measurement item in which to store the number of measurements performed by the measurement unit 41; and a result item in which to store whether or not an obtained measurement result is a final result. It should be noted that, in FIG. 7A, in each column of the result item, characters indicating that "final" or "not final" are shown for convenience. Actually, however, a flag indicating "final" or "not final" is held in each column of the result item.

As described above, the information processing unit 42 has received the rack ID and sample IDs from the transport controller 5 upon a sample rack L being pushed out onto the transport path 311 of the right table 310. When the sample rack L is transported along the measurement line and a sample container T to be subjected to measurement by the measurement unit 41 is detected by the container sensor 322, the information processing unit 42 registers this sample in the sample information table.

When a sample is registered in the sample information table, the number-of-measurement item becomes "0", and the result item becomes "not final". Then, when a first-round test on the sample is performed, the number-of-measurement item becomes "1". When it is determined that a first retest is not necessary based on the measurement result of the first-round test, the result item becomes "final". Further, when a first retest on the sample is completed, the number of measurements becomes "2", and the result item becomes "final". How the states of the number-of-measurement item and the result item change will be described later with reference to FIGS. 8, 9A, and 9B.

FIG. 7B shows a concept of a configuration of the priority table.

The priority table shows the priority orders of samples to be supplied to the measurement unit 41. When each sample container T to be subjected to measurement by the measurement unit 41 has been detected by the container sensor 322, the information processing unit 42 registers samples in the priority table, in the order of their detection. Accordingly, as shown in FIG. 7B, for example, a sample registered earlier is positioned higher, and a sample registered later is positioned lower. FIG. 7B shows an example of the priority table when sample containers T are held in all of the 10 holding positions in a sample rack L. How the state of the priority table changes will be described later with reference to FIGS. 8, 9A, and 9B.

Figure 8:
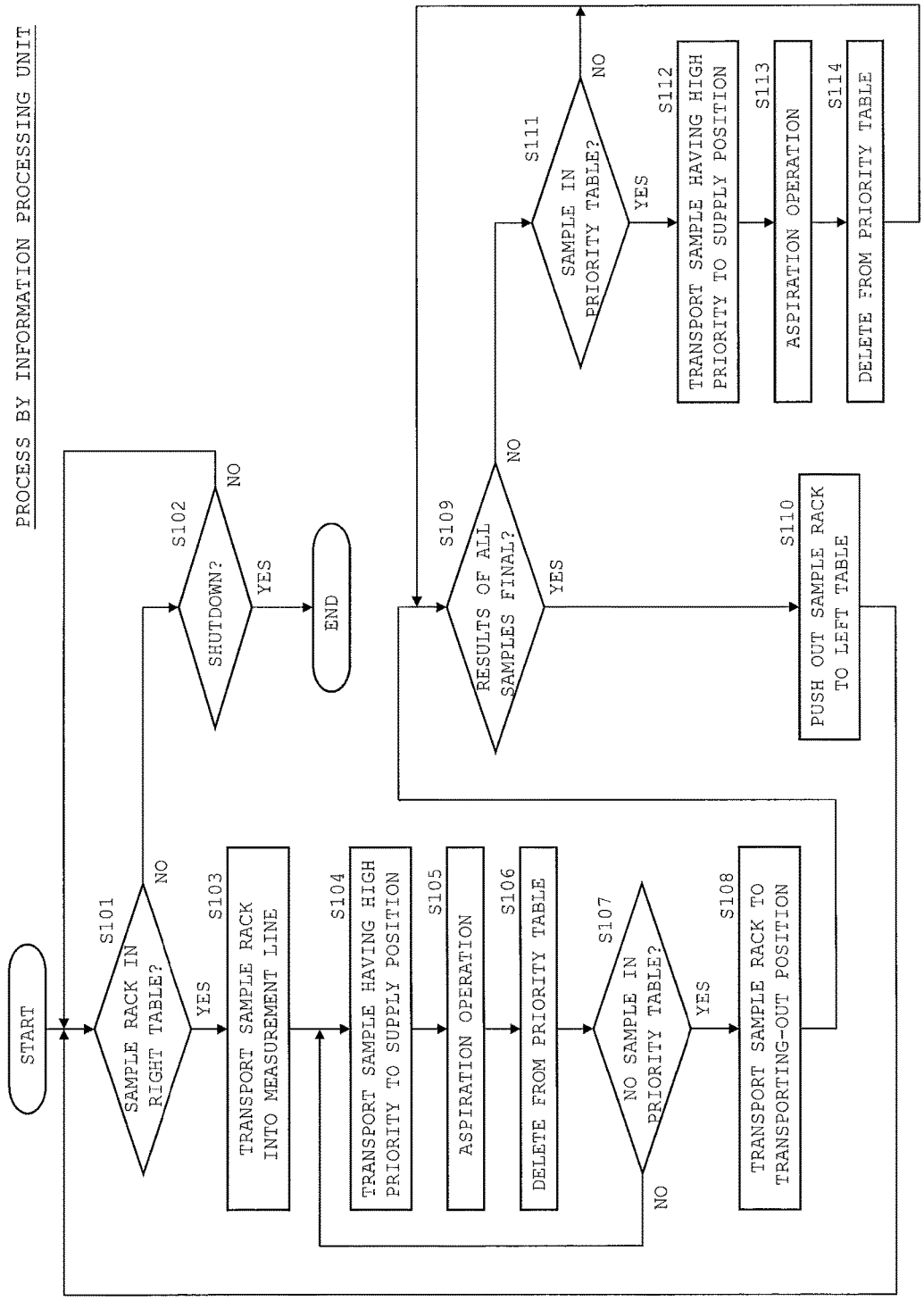
FIG. 8 is a flow chart showing measurement operation performed by an information processing unit according to an embodiment.

FIG. 8 is a flow chart showing measurement operation performed by the information processing unit 42.

When the control section 421 of the information processing unit 42 has determined that there is a sample rack L on the right table 310 by means of the sensors 312a and 312b (S101: YES), the control section 421 causes the rack sending-in mechanism 313 to send the sample rack L into the rack transporter 320 (measurement line) (S103). The sample rack L sent into the measurement line is transported leftward as appropriate, and the container sensor 322 detects presence/absence of sample containers T held in the sample rack L. Accordingly, each sample is registered in the sample information table and the priority table.

It should be noted that the determination of whether there is a sample rack L on the right table 310 (S101) is repeated until a shutdown process of the information processing unit 42 is performed (S102: YES).

Subsequently, based on the priority table, the control section 421 causes a sample container T having the highest priority to be transported to the supply position (S104). When the sample container T is located at the supply position, the control section 421 causes the measurement unit 41 to take this sample container T inside, and causes the sample to be aspirated from the sample container T (S105). When the aspiration has been completed, the control section 421 returns this sample container T to its original holding position in the sample rack L, and deletes this sample from the priority table (S106). It should be noted that when the aspiration of the sample has been completed, the control section 421 performs measurement and analysis in parallel with aspiration operation of other samples.

Subsequently, the control section 421 determines whether there is no sample in the priority table (S107). For example, when aspiration operation of samples has been sequentially advanced, the samples are sequentially deleted from the priority table in S106. Thus, all samples are deleted from the priority table in the end. Further, even in the case of a sample for which the aspiration was already completed and that was deleted from the priority table, if it is determined that a first retest is necessary, this sample will be added to the priority table again, as described later. At this time, the sample rack L is transported rightward on the measurement line, by the belt 321a or 321b being driven rightward. As a result, its sample container T is located at the supply position. While repeating measurement in this manner, the control section 421 repeats the processes of S104 to S106 until it is determined that there is no sample in the priority table (S107: YES). When there is no sample in the priority table (S107: YES), the control section 421 causes this sample rack L to be transported to a left end position (transporting-out position) of the rack transporter 320 (S108).

At the timing when there is no longer any sample in the priority table in S107, there are cases where there remains sample(s) for which necessity/unnecessity of a first retest has not been determined yet. In such a case, if it is determined that a first retest is necessary for one or more of the remaining sample(s) for which necessity/unnecessity has not been determined yet, such sample(s) are registered again in the priority table which was determined as having no sample in S107. In this case, it is determined as YES in S111 which is described later, and the sample(s) are subjected to processing. On the other hand, in a case where it is determined that a first retest is necessary for none of the remaining sample(s) for which necessity/unnecessity has not been determined yet, the priority table which was determined as having no sample in S107 remains in the state with no samples.

Next, by referring to the sample information table, the control section 421 determines whether the result items of all the samples held in this sample rack L are "final" (S109). When all the result items are "final" (S109: YES), the control section 421 causes this sample rack L to be pushed out to the left table 330 (S110), and returns the processing to S101. On the other hand, when all the result items are not "final" (S109: NO), the control section 421 determines again whether sample(s) of the sample rack L have been registered in the priority table (S111). It should be noted that the procedure of a result item being changed from "not final" of the initial state to "final" will be described later with reference to FIG. 9A.

When there are sample(s) in the priority table (S111: YES), the control section 421 causes a sample container T having the highest priority to be transported to the supply position (S112). Also at this time, the sample rack L is transported rightward on the measurement line, by the belt 321a or 321b being driven rightward. As a result, its sample container T is located at the supply position.

Subsequently, the control section 421 causes the sample to be aspirated from this sample container T (S113), deletes this sample from the priority table (S114), and returns the processing to S109. Also in this case, when the aspiration of the sample has been completed, the control section 421 performs measurement and analysis in parallel with aspiration operation of other samples. On the other hand, also when there is no sample in the priority table (S111: NO), the control section 421 returns the processing to S109. It should be noted that, after the processing is returned to S109, if it is determined as NO in S109 and further determined as NO in S111, the sample rack L is transported to the transporting-out position again. In this manner, measurement is repeated until the result items of all the samples become "final".

Figure 9B:
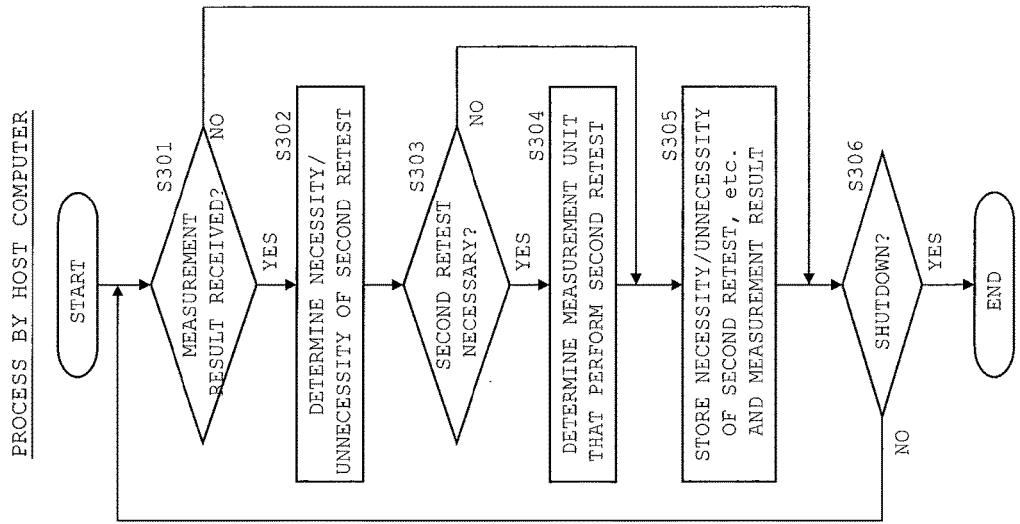
FIG. 9B is a flow chart showing a process of determining necessity/unnecessity of a second retest performed by a host computer, according to an embodiment.
Figure 9A:
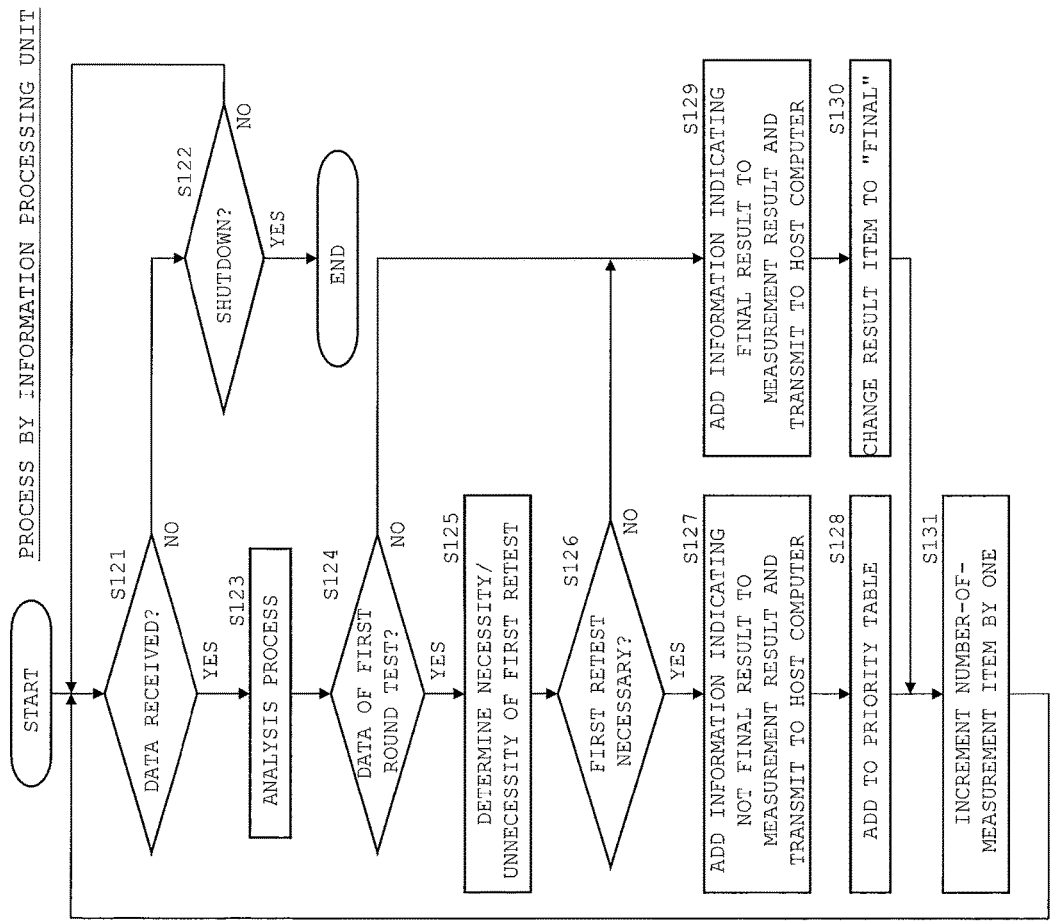
FIG. 9A is a flow chart showing a process performed by an information processing unit using data of samples obtained by a measurement unit.

FIG. 9A is a flow chart showing a process performed by the information processing unit 42 using data of samples obtained by the measurement unit 41.

When the control section 421 of the information processing unit 42 has received data of a sample from the measurement unit 41 (S121: YES), the control section 421 performs an analysis process based on the received data (S123). It should be noted that the determination of whether data has been received from the measurement unit 41 (S121) is repeated until a shutdown process of the information processing unit 42 is performed (S122: YES).

Subsequently, the control section 421 determines whether the data received in S121 is data obtained through a first-round test (S124). Specifically, the control section 421 refers to the sample information table with respect to the sample being the source of the data. When the number of measurements is "0", the control section 421 determines that the data is data obtained through a first-round test, and when the number of measurements is "1", the control section 421 determines that the data is not data obtained through a first-round test.

When the data received in S121 is data of a first-round test (S124: YES), the control section 421 determines necessity/unnecessity of a first retest based on the measurement result obtained in S123 (S125). It should be noted that determination conditions used for determining necessity/unnecessity of a first retest are stored in the hard disk 423 of the information processing unit 42, associated with the respective measurement units 41. In the determination of necessity/unnecessity of a first retest, when a numerical value of each measurement item, such as red blood cell count or white blood cell count, obtained in the analysis process of S123 is outside a predetermined range, it is determined that a first retest is necessary. This determination process is performed without using test information other than the measurement result obtained in S123.

As the determination condition used for determining necessity/unnecessity of a first retest, a retest rule "IF WBC>100 THEN Retest (DIFF)" is set, for example. Such a rule is described as an IF-THEN statement. In the IF part (condition part), presence/absence of occurrence of a predetermined fact is set, and in the THEN part, an action command to execute a retest is set. In this example, if the measurement result of WBC is greater than 100, execution of a retest of the DIFF item is instructed. In a case where a retest rule "IF RBC<30 THEN Retest (CBC)" is set, for example, if the measurement result of RBC is smaller than 30, execution of a retest of the CBC item is instructed.

As a result of the determination of necessity/unnecessity of a first retest, when it has been determined that a first retest is necessary for this sample (S126: YES), the control section 421 adds information indicating that the measurement result is not a final result, to the measurement result of this sample, and transmits this measurement result to the host computer 6 (S127). Further, the control section 421 adds this sample to the priority table (S128), and increments by one the number-of-measurement item of the sample information table (S131). Here, in a case where a sample at the highest order in the priority table is being subjected to the aspiration operation, the sample to be added in S128 is added in the second order from the top of the priority table. In a case where a sample at the highest order in the priority table is not being subjected to the aspiration operation, the sample to be added in S128 is added at the highest order in the priority table. As a result, the sample for which it has been determined that a first retest is necessary is subjected to aspiration and measurement in advance of other samples.

On the other hand, when the measurement result received in S121 is not a measurement result of a first-round test (S124: NO), or when it has been determined that a first retest is not necessary for this sample (S126: NO), the control section 421 adds information indicating that the measurement result is the final result, to the measurement result of the sample, and transmits this measurement result to the host computer 6 (S129). It should be noted that, in the present embodiment, the number of first retests to be performed based on a first-round test is 1 at maximum.

Subsequently, the control section 421 changes the result item of this sample in the sample information table to "final" (S130), and further, increments by one the number-of-measurement item in the sample information table (S131). Then, when the result items of all the samples held in this sample rack L become "final", it is determined as YES in S109 in FIG. 8, and this sample rack L is pushed out from the measurement line to the left table 330.

FIG. 9B is a flow chart showing a process of determining necessity/unnecessity of a second retest performed by the host computer 6.

When the control section 601 of the host computer 6 has received a measurement result from the information processing unit 42 in S127 and S129 (S301: YES), the control section 601 determines necessity/unnecessity of a second retest for this sample (S302). When it has been determined that a second retest is necessary (S303: YES), the control section 601 determines a measurement unit 41 that performs the second retest (S304). The determination of necessity/unnecessity of a second retest and the determination of a measurement unit 41 that performs the second retest are performed in accordance with a predetermined determination condition, based on test information including past measurement results, disease information, and the like of the patient from whom this sample was collected, and based on all measurement items that can be measured by the three measurement units 41. Such test information and measurement items are stored in advance in the hard disk 603. In this process, for example, with respect to a specific measurement item, a current measurement result (current value) and a preceding measurement result (preceding value) are compared with each other, and the difference between them is compared with a reference value. Thereby, when the difference between the current value and the preceding value is greater than or equal to the reference value, it is determined that the current value is not reliable, and it is determined that a retest is necessary for the same measurement item as that of the current measurement result. Further, among the measurement units 41 that can measure the measurement item for which it was determined that a retest is necessary, a measurement unit 41 that will suffer less measurement load is determined as the measurement unit 41 that performs the second retest.

As the determination condition stored in the host computer 6, a retest rule "IF Anemia? THEN Retest (RET)" is set, for example. In this example, if disease information indicating that the subject has anemia is stored in the host computer 6, execution of a retest for RET is instructed. In a case where a retest rule "IF WBC (this time)–WBC (last time)>30 THEN Retest (DIFF)" is set, the current WBC measurement result (current value) and the preceding WBC measurement result (preceding value) are compared with each other. When the difference between them is greater than or equal to a reference value, it is determined that the current value is not reliable, and execution of a retest for the DIFF item which includes WBC as the measurement item is instructed.

Subsequently, the control section 601 stores necessity/unnecessity of a second retest obtained in S302, information indicating the measurement unit 41 that performs the second retest when it was determined that the second retest is necessary, and the measurement result, in the hard disk 603 (S305). The processes of S301 to S305 are repeated until a shutdown process of the host computer 6 is performed (S306: YES).

It should be noted that the determination condition used by the information processing unit 42 for determining necessity/unnecessity of a first retest and the determination condition used by the host computer 6 for determining necessity/unnecessity of a second retest can be set by the user as desired. The user can set the determination condition for determining necessity/unnecessity of a first retest for each measurement unit 41, within the measurement items measurable by the measurement unit 41. For example, in the present embodiment, among the three measurement units 41, the measurement units 41 at the right end and in the middle can perform measurement regarding the CBC item and the DIFF item. Therefore, for these measurement units 41, the determination condition for determining necessity/unnecessity of a first retest can be set within the CBC item and the DIFF item. The measurement unit 41 at the left end can perform measurement regarding the RET item, in addition to the CBC item and the DIFF item. Therefore, for this measurement unit 41, the determination condition for determining necessity/unnecessity of a first retest can be set within the CBC item, the DIFF item, and the RET item. In the host computer 6, the determination condition for determining necessity/unnecessity of a second retest can be set within the CBC item, the DIFF item, and the RET item. In this case, the user can set the determination condition for determining necessity/unnecessity of a second retest, including not only these measurement items, but also the history of past measurement results of the patient, and the like.

FIG. 10A is a flow chart showing a process performed by the transport controller 5 when a sample rack L is transported into the left table 330 in S110 in FIG. 8.

When the control section 501 of the transport controller 5 has detected a sample rack L on the transport path 331 of the left table 330 by means of the sensors 332a and 332b (S201: YES), the control section 501 makes an inquiry about necessity/unnecessity of a second retest to the host computer 6, with respect to sample(s) which have been subjected to measurement by the measurement unit 41 among the samples held in this sample rack L (S203). It should be noted that the determination of whether a sample rack L on the transport path 331 has been detected (S201) is repeated until a shutdown process of the transport controller 5 is performed (S202: YES).

Upon receiving necessity/unnecessity of a second retest from the host computer 6 (S204: YES), the control section 501 determines whether there are sample(s) for which a second retest is necessary among the samples held in the sample rack L, based on the content of the received information (S205). When there are sample(s) for which a second retest is necessary (S205: YES), the control section 501 causes this sample rack L to be transported to the measurement unit 41 of the subsequent stage (S206). On the other hand, when there is no sample for which a second retest is necessary (S205: NO), the control section 501 causes this sample rack L to be sent into the collection line to be transported to the collection unit 21 (S207).

FIG. 10B is a flow chart showing a process of transmitting necessity/unnecessity of a second retest performed by the host computer 6.

When the control section 601 of the host computer 6 has received an inquiry about necessity/unnecessity of a second retest from the transport controller 5 (S311: YES), the control section 601 transmits, with respect to this sample, necessity/unnecessity of a second retest stored in the hard disk 603, and information indicating the measurement unit 41 that performs the second retest when the second retest is necessary, to the transport controller 5 (S312). The processes of S311 to S312 are repeated until a shutdown process of the host computer 6 is performed (S313: YES).

As described above, according to the present embodiment, when it has been determined that a retest (first retest) needs to be performed by the measurement unit 41 that performed the first-round test, the sample rack L located on the measurement line of that measurement unit 41 is transported in the left-right direction along the measurement line as appropriate, and the sample is supplied to the measurement unit 41. Here, the determination regarding the first retest is performed by the control section 421 of the information processing unit 42, and thus, performed quickly. Accordingly, the retest (first retest) of the sample can be quickly performed.

Further, with respect to all the samples held in the sample rack L located on the measurement line of the measurement unit 41, when the result item has become "final" and it has been determined that a retest (first retest) is unnecessary, this sample rack L is pushed out from the measurement line to the left table 330. Also in this case, the determination whether the result item is "final" and the determination regarding the first retest are performed by the control section 421 of the information processing unit 42, and thus, performed quickly. Accordingly, the sample rack L which has been subjected to processing is quickly pushed out from the measurement line to the left table 330. Thus, another sample rack L can be quickly transported into the measurement line.

Further, with respect to sample(s) in the sample rack L pushed out to the left table 330, when it has been determined that a retest (second retest) needs to be performed by another measurement unit 41, the sample rack L is transported to said another measurement unit 41 on the downstream side (left side) to be subjected to a retest (second retest). Accordingly, even a retest that cannot be performed by the measurement unit 41 that performed the first-round test can be assuredly performed by said another measurement unit 41. Here, the determination regarding the second retest is performed by the control section 601 of the host computer 6, based on past test information and all measurement items that can be measured by the three measurement units 41. Accordingly, the determination can be performed with respect to all the measurement items, without any omission, and it is possible to determine to which measurement unit 41 the sample should be transported. Further, while the sample rack L is retained in the left table 330, the sample rack L does not hinder transportation of another sample rack L on the measurement line or the supply line. Thus, even when the determination by the host computer 6 takes time, it is possible to suppress the sample processing efficiency from being reduced.

Further, according to the present embodiment, the control section 421 of the information processing unit 42 transmits each measurement result to the host computer 6 irrespective of necessity/unnecessity of a first retest (S127 and S129 of FIG. 9A). Accordingly, the host computer 6 can determine necessity/unnecessity of a second retest in advance. Thus, it is possible to reduce the waiting time from the time when the control section 501 of the transport controller 5 makes an inquiry about necessity/unnecessity of a second retest (S203 of FIG. 10A) to the time when it obtains necessity/unnecessity of a second retest.

An embodiment of the present invention has been described. However, the embodiment of the present invention is not limited thereto.

For example, in the above embodiment, a subject to be measured is exemplified by blood, but a subject to be measured may be urine. That is, the present invention can also be applied to a sample analysis system for testing urine, and further, the present invention can be applied to a clinical sample analysis system for testing other clinical samples.

Further, in the above embodiment, a transport system is configured by connecting the transporting units 31 to 33 each other which correspond to the measurement units 41, respectively. However, one transporting apparatus may be used in which the sample relaying section 3a and the sample supplying section 3b are provided in a region corresponding to each of the measurement units 41.

Further, in the above embodiment, each of the transporting units 31 to 33 is configured as divided into the sample relaying section 3a and the sample supplying section 3b. However, the preset invention is not limited thereto. The sample relaying section 3a and the sample supplying section 3b may be integrally provided.

Further, in the above embodiment, transportation of a sample rack L in the right table 310 and the rack transporter 320 is controlled by the information processing unit 42. However, the present invention is not limited thereto. A unit or an apparatus other than the information processing unit 42, such as the transport controller 5, may control the transportation.

Further, in the above embodiment, transportation of a sample rack L in the left table 330, and the rack transporters 340 and 350 is controlled by the transport controller 5. However, the present invention is not limited thereto. A unit or an apparatus other than the transport controller 5, such as the information processing unit 42, may control the transportation.

Further, in the above embodiment, a sample rack L placed in the feeding unit 22 is transported in the downstream direction (leftward) toward the measurement units 41. Then, when measurement is completed, the sample rack L is transported in the upstream direction (rightward) to be collected in the collection unit 21 which is provided to the feeding unit 22 side. However, the present invention is not limited thereto. When the measurement is completed, the sample rack L may be transported in the downstream direction (leftward) to be collected in a collection unit which is provided to the immediate left of the transporting unit 33. Also in this case, as in the above embodiment, it is configured such that the sample rack L is collected through the collection lines of the transporting units 31 to 33.

It should be noted that the number of the sample racks L located at the rack transporter 320 shown in FIG. 3 is not necessarily one. It may be configured such that two sample racks L are simultaneously located on the rack transporter 320, and the sample racks L are moved in parallel to each other by the two belts 321a and 321b, whereby the sample in each sample rack L is processed.

Further, in the above embodiment, upon completion of the analysis process of a sample, the information processing unit 42 immediately transmits the measurement result to the host computer 6. However, the present invention is not limited thereto. The information processing unit 42 may transmit the measurement result to the host computer 6, at the timing when the sample rack L is pushed out from the measurement line (the rack transporter 320) to the left table 330.

Further, in the above embodiment, one information processing unit 42 is provided as the computer that obtains data of samples obtained by the three measurement units 41 and performs the analysis process. However, the present invention is not limited thereto. As the computer for performing the analysis process, three information processing units may be provided so as to correspond to the three measurement units 41.

Further, in the above embodiment, determination regarding the first retest is performed by the information processing unit 42, and determination regarding the second retest is performed by the host computer 6. However, the present invention is not limited thereto. A part of the determination regarding the first retest may be performed by the host computer 6, and a part of the determination regarding the second retest may be performed by the information processing unit 42.

In addition to the above, various modifications can be made as appropriate to the embodiment of the present invention without departing from the scope of the technical idea defined by the claims.

What is claimed is:

1. A sample testing system, comprising:
a computer; and
a sample analysis system physically separate from and in communication with the computer via a communication network, the sample analysis system, comprising:
a first measurement unit comprising a first detector having a structure to perform a measurement on a sample;
a second measurement unit that is arranged at a downstream side of the first measurement unit, wherein the second measurement unit comprises a second detector having a structure to perform a measurement on the sample;
a transporting apparatus comprising:
a first transporting unit arranged corresponding to the first measurement unit; and
a second transporting unit arranged corresponding to the second measurement unit; and
a controller connected to the first measurement unit and the second measurement unit and wherein the communication between the computer and the sample analysis system is accomplished by the controller being connected to the computer via the communication network;
wherein the first transporting unit comprises:
a first transport belt that transports a sample container to a transporting-out position via a first sample supply position for the first measurement unit;
a sending-out belt that sends out the sample container to the downstream side of the first measurement unit; and
a table arranged between the first transport belt and the sending-out belt, wherein the table retains the sample container transported out from the transporting-out position;
wherein the second transporting unit comprises: a second transport belt that transports the sample container sent out from an upstream side of the second measurement unit to a second sample supply position for the second measurement unit; and
wherein the controller comprises a structure that:
receives measurement data regarding a compositional property of the sample by the first measurement unit, and obtains a measurement result comprising a numerical value for a measurement item by analyzing the received measurement data;
determines whether or not the obtained numerical value is outside a predetermined range;
causes the sample container containing the sample measured by the first measurement unit to wait at the transporting-out position until obtaining a determination result of whether or not the obtained numerical value is outside the predetermined range;
controls the first transport belt to transport the sample container containing the sample measured by the first measurement unit from the transporting-out position to the first sample supply position when the obtained numerical value is outside the predetermined range and then controls the first measurement unit to perform a measurement of the sample;
controls a pushing-out mechanism to push the sample container containing the sample measured by the first measurement unit from the transporting-out position out to the table when the obtained numerical value is within the predetermined range, and makes an inquiry to the computer whether or not the sample needs to be measured by the second measurement unit;
causes the sample container to be retained by the table until receiving, from the computer, a determination result of whether or not measurement by the second measurement unit is necessary for the sample in the sample container transported out to the table; and
controls the sending-out belt and the second transport belt to transport the sample container retained by the table to the second sample supply position upon receiving a determination result that the sample needs to be measured by the second measurement unit from the computer and then controls the second measurement unit to perform the measurement of the sample;
wherein the computer determines, based on the measurement of the sample measured by the first measurement unit and other test information stored in the computer, whether or not the sample measured by the first measurement unit needs to be measured by the second measurement unit.

2. The sample testing system according to claim 1, wherein the other test information stored in the computer includes a past measurement result of the sample measured by the first measurement unit.

3. The sample testing system according to claim 1, wherein the first measurement unit is capable of measuring the sample for a first measurement item, and the second measurement unit is capable of performing measurement for a second measurement item in addition to the first measurement item.

4. The sample testing system according to claim 3, wherein the computer has stored therein all measurement items measurable by the first measurement unit and the second measurement unit, and determines, based on the measurement result of the sample measured by the first measurement unit and based on the other test information and the all measurement items stored in the computer, whether the sample measured by the first measurement unit needs to be measured by the second measurement unit.

5. The sample testing system according to claim 4, wherein the controller is configured to be able to set a determination condition based on which the controller determines whether or not a retest is necessary, within measurement items measurable by the first measurement unit, and the computer is configured to be able to set a determination condition based on which the computer determines whether or not a retest is necessary, within measurement items measurable by the first measurement unit and the second measurement unit.

6. The sample testing system according to claim 1, wherein the first transporting unit further comprises a container mover that moves out the sample container retained in the table to the sending-out belt side,
   wherein the controller comprises a structure that controls the container mover to move out the sample container waiting in the table, from the table to the sending-out belt upon receiving, from the computer, a determination result indicating that the measurement by the second measurement unit is necessary for the sample in the sample container transported out to the table, and
   the sending-out belt sends out the sample container transported out from the table to the downstream side of the first measurement unit.

7. The sample testing system according to claim 1, wherein the controller has stored therein, for each measurement unit, a determination condition for determining whether or not a retest by a corresponding measurement unit is necessary, and when the measurement result of the sample measured by the first measurement unit satisfies the determination condition corresponding to the first measurement unit, the controller determines that a retest by the first measurement unit is necessary.

8. The sample testing system according to claim 1, wherein when a retest of the sample measured by the first measurement unit has been performed by the first measurement unit, the computer determines whether or not measurement of the sample by the second measurement unit is necessary, based on a measurement result of the retest by the first measurement unit.

9. The sample testing system according to claim 1, comprising a transporting-in unit which transports a sample container into the transporting apparatus, wherein the first measurement unit is located to the transporting-in unit side, and the second measurement unit is located to the downstream side of the first measurement unit relative to the transporting-in unit.

10. The sample testing system according to claim 1, wherein the first-transporting unit comprises:
    as the sending-out belt, a third transport belt capable of receiving a sample container transported out from the upstream side of the first measurement unit and capable of transporting out the sample container to the downstream side of the first measurement unit, and
    a second pushing-out mechanism capable of transferring a sample container on the third transport belt to the first transport belt.

11. The sample testing system according to claim 1, comprising: a collection unit comprising a belt to receive a sample container for which measurement has been completed, from the transporting apparatus, and a second table on which the received sample container is placed;
    wherein each of the first and second transporting units comprises a fourth transport belt for transporting the sample container for which measurement has been completed, to the collection unit side, and
    the controller causes the sample container for which the computer has determined that measurement by the second measurement unit on the downstream side is unnecessary, to be transported to the collection unit by use of at least one of the fourth transport belts.

12. The sample testing system according to claim 1, wherein the transporting apparatus is configured to transport a sample rack holding a plurality of sample containers, and
    the controller determines, while a sample in one sample container held in the sample rack is being measured by the first measurement unit, whether or not a retest by the first measurement unit is necessary for a sample in another sample container held in the sample rack.

13. The sample testing system according to claim 1, wherein the controller comprises:
    a first determination controller which determines, based on a measurement result of a sample measured by the first measurement unit, whether or not a retest of the sample by the first measurement unit is necessary, and determines, based on a measurement result of a sample measured by the second measurement unit, whether or not a retest of the sample by the second measurement unit is necessary, and
    a second determination controller which receives, from the computer, a determination result of whether or not measurement by the second measurement unit is necessary for the sample measured by the first measurement unit, wherein the first determination controller controls operation of the first measurement unit and the second measurement unit and the first transport belt of the first transporting unit and the second transport belt of the second transporting unit, and the second determination controller controls operation of the sending-out belt.

14. The sample testing system according to claim 1, comprising:
    a third measurement unit arranged to the downstream side of the first measurement unit, wherein
    the transporting apparatus comprises a third transporting unit arranged corresponding to the third measurement unit,
    the computer determines, based on the measurement result of the sample measured by the first measurement unit and other test information stored therein, whether or not the sample measured by the first measurement unit needs to be measured by either one of the second measurement unit and the third measurement unit, and
    the controller has a structure to perform a process of transmitting the measurement result of the sample measured by the first measurement unit, to the computer, and a process of receiving a determination result of whether or not the sample needs to be measured by either one of the second measurement unit and the third measurement unit, from the computer.

15. The sample testing system according to claim 1, wherein the controller comprises one computer apparatus which receives and analyzes measurement data from each of the measurement units and controls each of the measurement units and the transport belt of each of the transporting units.

16. The sample testing system according to claim 1, wherein the controller comprises a first controller corresponding to the first measurement unit, and a second controller corresponding to the second measurement unit.

* * * * *